United States Patent [19]

Mather, III et al.

[11] 4,424,190

[45] Jan. 3, 1984

[54] RIGID SHELL EXPANSIBLE BLOOD RESERVOIR, HEATER AND HOLLOW FIBER MEMBRANE OXYGENATOR ASSEMBLY

[75] Inventors: Frank W. Mather, III, Pleasant Hill; Andreas Preussner, Berkeley, both of Calif.; Gaylord L. Berry, Salt Lake City, Utah

[73] Assignee: Cordis Dow Corp., Miami, Fla.

[21] Appl. No.: 350,664

[22] Filed: Feb. 22, 1982

[51] Int. Cl.³ ............................................ A61M 1/03
[52] U.S. Cl. ...................................... 422/46; 55/158; 210/321.4; 210/497.1; 422/48; 422/310; 604/403; 604/408
[58] Field of Search ....................... 422/44, 45, 46, 48, 422/310; 55/16, 158, DIG. 45; 210/646, 321.3, 321.4, 321.5, 456, 497.1; 128/214 D, 272, 272.3, DIG. 3; 604/403, 408

[56] References Cited

U.S. PATENT DOCUMENTS

| | | | |
|---|---|---|---|
| 3,536,611 | 10/1970 | De Filippi et al. | 210/646 |
| 3,557,962 | 1/1971 | Kohl | 210/500.2 |
| 3,794,468 | 2/1974 | Leonard | 422/48 |
| 3,907,504 | 9/1975 | Hammond et al. | 422/48 X |
| 3,957,648 | 5/1976 | Roget et al. | 210/321.3 |
| 3,985,135 | 10/1976 | Carpenter et al. | 128/214 D |
| 3,998,593 | 12/1976 | Yoshida et al. | 422/46 |
| 4,020,230 | 4/1977 | Mahoney et al. | 55/16 X |
| 4,026,669 | 5/1977 | Leonard et al. | 422/44 |
| 4,140,637 | 2/1979 | Walter | 210/321.1 |
| 4,326,526 | 4/1982 | Buck et al. | 128/272 |

FOREIGN PATENT DOCUMENTS 2617208 7/1977 Fed. Rep. of Germany ........ 422/46

Primary Examiner—Barry S. Richman
Attorney, Agent, or Firm—Neal A. Waldrop; Jay C. Taylor

[57] ABSTRACT

A closed, air-free blood oxygenator assembly having integrated into one self-supporting unit a rigid-shell blood reservoir having an easily visible, concavity which is closed by an attached expansible, flexible membrane which overlies the concavity and forms a variable volume liquid and air-tight blood reservoir, and an attached blood heater, and a hollow fiber membrane oxygenator. The assembly stores, heats, oxygenates and purifies blood by passing oxygen through the lumens of a mat of small diameter gas-permeable hollow fibers supported on a cylindrical core as blood flows over the outside surfaces of the fibers in a small, easy to use, safe, integrated unit which avoids blood contact with ambient air as blood circulates through the assembly during surgery.

14 Claims, 9 Drawing Figures

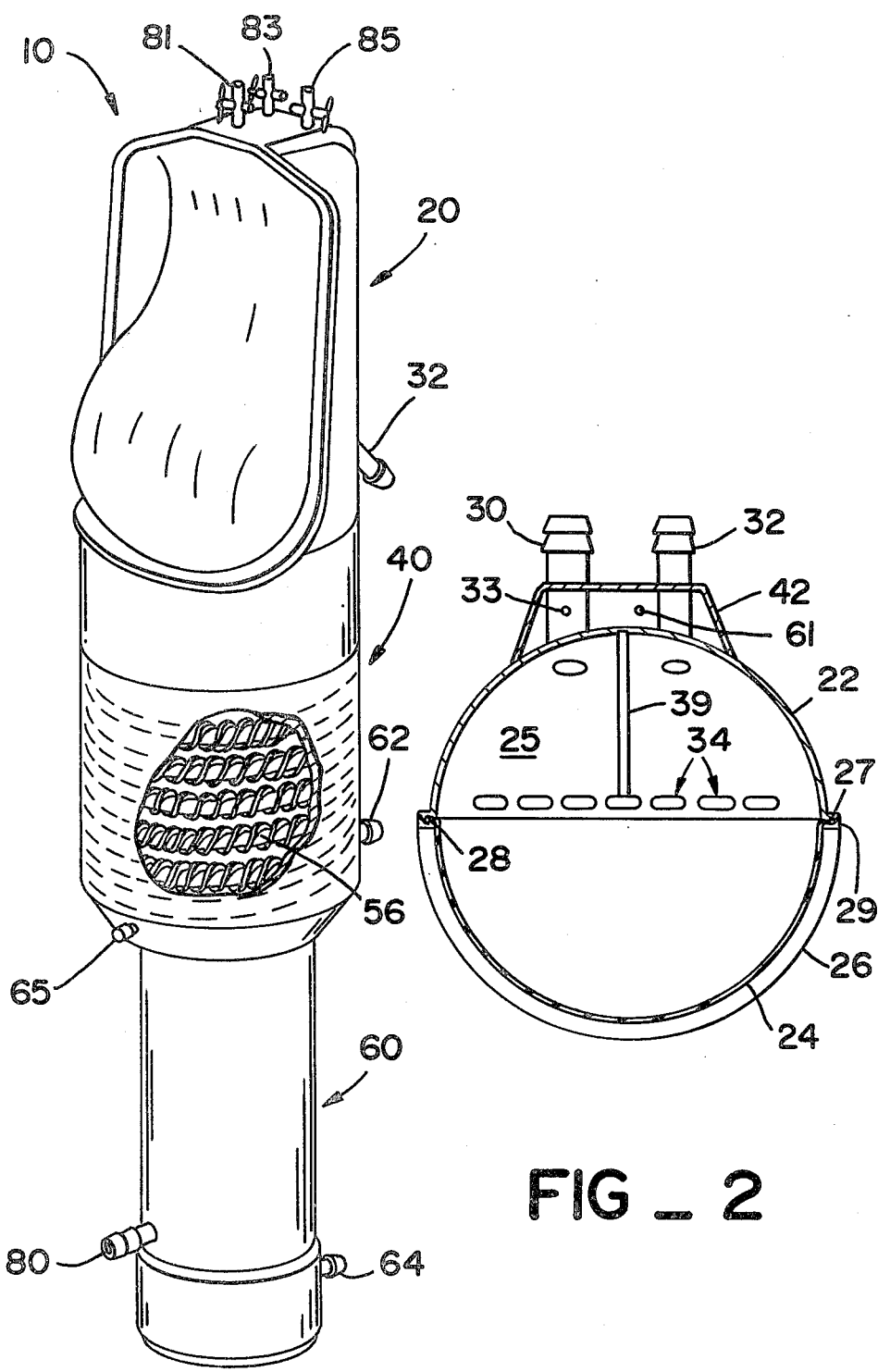
FIG_1
FIG_2

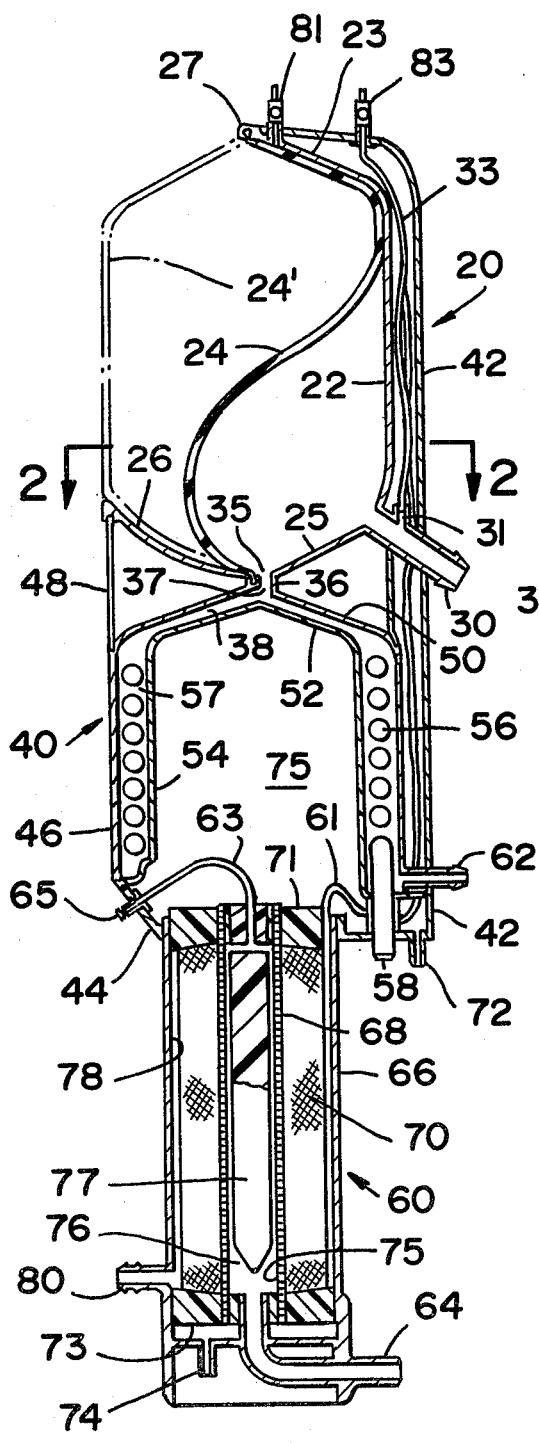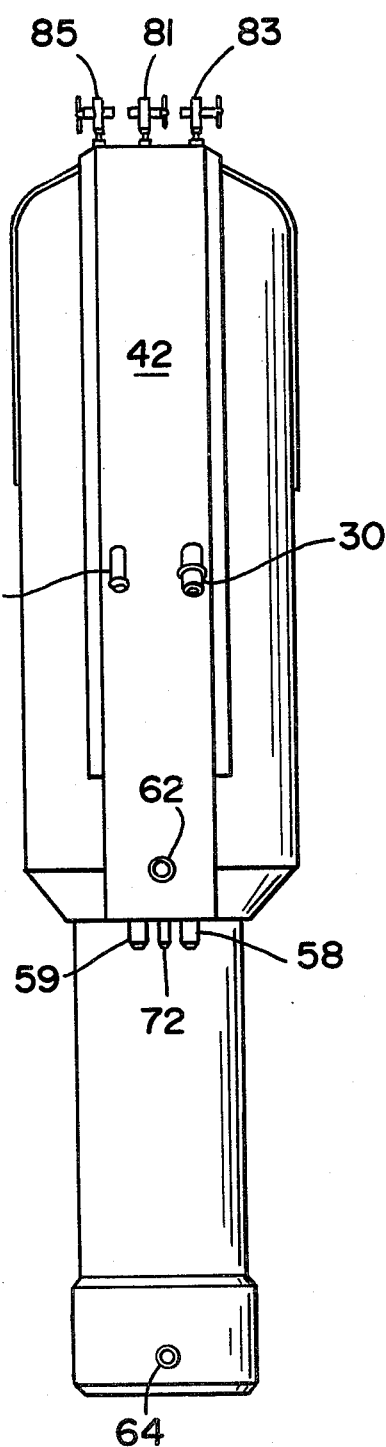
FIG_3          FIG_4

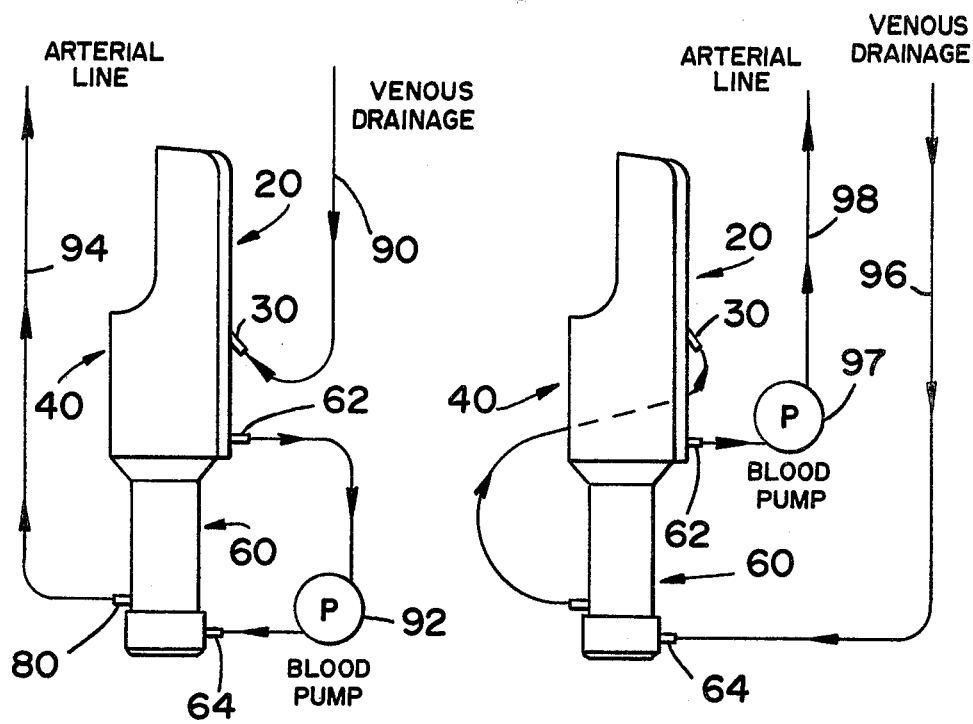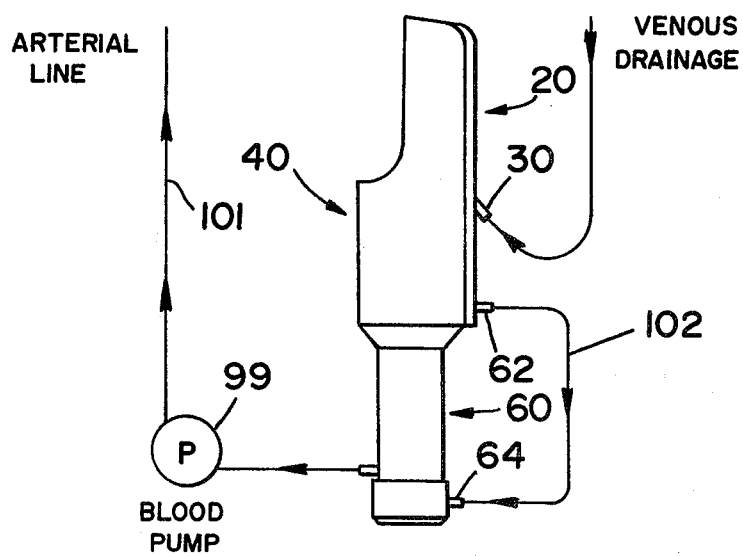

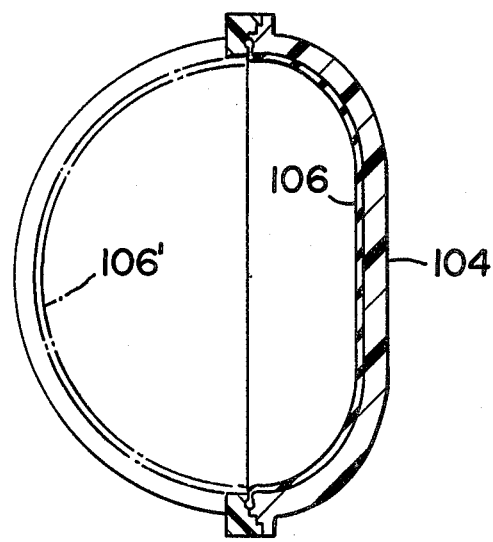
FIG_8
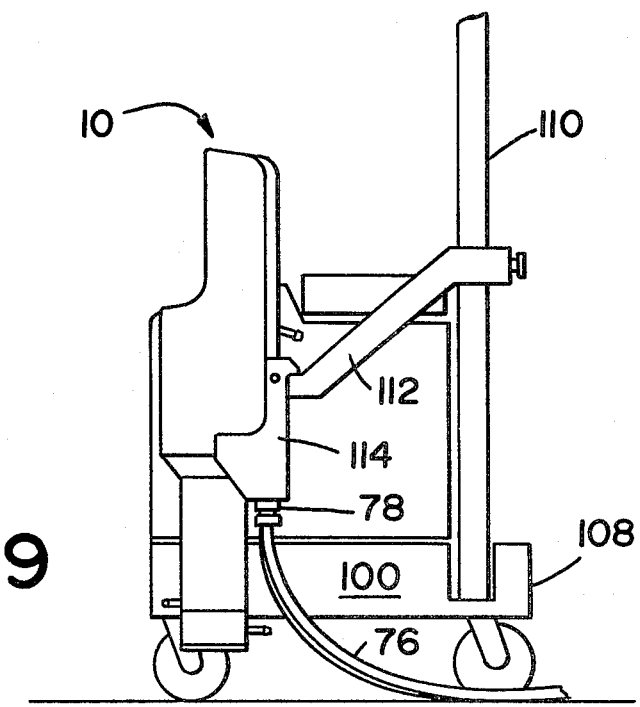
FIG_9

RIGID SHELL EXPANSIBLE BLOOD RESERVOIR, HEATER AND HOLLOW FIBER MEMBRANE OXYGENATOR ASSEMBLY

BACKGROUND OF THE INVENTION

This invention relates to improved blood oxygenation apparatus for use in oxygenating blood during surgery on vital organs, particularly heart surgery.

The apparatus is a self-supporting assembly which integrates into one unit a new blood reservoir, a blood heater and a new hollow fiber membrane blood oxygenator. The blood heater is located between the upper blood reservoir and lower exygenator and the assembly provides a closed-to-air circuit of blood flow which includes the necessary flow means and connectors to enable the assembly to store, oxygenate and provide the desired temperature to blood passing through the assembly.

Blood heaters, blood reservoirs and membrane oxygenators of various types are known and have been used in the past in the oxygenation of blood during surgery. Different types of blood heaters useful in extracorporeal circulation are surveyed in the book entitled *Heart-Lung Bypass* by Pierre M. Galletti, M.D., et al. at pages 165–170; improved configurations making use of heaters having helically fluted aluminum tubing wrapped around a supporting cylindrical core that are integral with a blood oxygenator are disclosed in U.S. Pat. Nos. 4,065,264, 4,138,288 and 4,138,464.

Membrane oxygenators making use of membranes in sheet form or large flattened tube form of the type disclosed in U.S. Pat. No. 3,757,955, are known and have been used in devices which interconnect such sheets, permeable to oxygen carbon dioxide and water vapor but impermeable to blood, in extracorporeal circuits such as those shown in U.S. Pat. Nos. 3,929,414 and 4,061,470; sheet membranes have also been integrated into a single unit having a heat exchanger and an open to air blood reservoir in U.S. Pat. No. 4,151,088.

Blood heat exchangers and blood containers of the open-to-air type, or of the pillow-shaped collapsible film type, normally suspend from a supporting stand adjacent to a separate heat exchanger and blood bubbler, are also known and shown in U.S. Pat. Nos. 4,058,369 and 4,205,042. Large, flattened permeable tubes made of polysulfones, polycarbonates and copolymers thereof suitable for oxygenation of blood or kidney dialysis are used in a combination apparatus having an integral heat exchanger that is shown in U.S. Pat. No. 4,094,792. The above identified patents constitute the closest known prior art to the inventions of the claims of this application.

There are disadvantages of a practical use nature, or of a functional nature, or of a safety nature that are known with respect to each of the above identified separate devices and assembled units. Importantly, it is a known and accepted disadvantage to a patient to expose blood to air in an extracorporeal circuit during surgery and devices which oxygenate blood by using air or oxygen in an open bubbler device suffer this defect. It is also known to be undesirable to subject blood to unusual mechanically applied forces of stress during flow through the reservoir, heater and/or oxygenator and that motions and treatment of blood in the extracorporeal circuit that closely approximate those normally experienced within the body are safest and best for the patient's welfare.

It is, therefore, the primary object of this invention to provide a unitary assembly of a new rigid reservoir, heater and a new hollow fiber blood oxygenator that avoids the disadvantages of prior oxygenator apparatus and provides operational advantages in the important categories of avoidance of blood quality deterioration due to mechanical stress and exposure to air in the extracorporeal circuit and enhances patient safety during oxygenation and storage outside the body during surgery.

SUMMARY OF THE INVENTION

The assembly of this invention comprises a rigid shell reservoir having novel attached compliant means forming, with a concavity defining portion of the shell, a self-supporting air tight and liquid tight expansible blood container. The reservoir is secured to one end of a blood heater of conventional design and a hollow fiber oxygenator is secured to the other end of the heater. Optionally, the three component units may be disengageably, or permanently attached to form one composite, integral unit. In either the disengageable or permanent assembly form use is normally in vertical array with the reservoir on top.

Internal blood flow channels, or tubing, are arranged within the assembly to permit venous blood from the patient or from a cardiotomy reservoir to enter first the expansible blood reservoir, or the hollow fiber oxygenator as selected, and then to pass through the other of the two units and the heater prior to return to the patient in oxygenated condition at the appropriate temperature to suite the patient's needs throughout the heart lung bypass procedure. Blood flow through the assembly is accomplished without contact with air. Oxygenation occurs at the thin line interface between the blood and the peripheral surfaces of the small hollow fibers as the blood flows through the gaps between fibers and makes contact with the peripheral surface of the fibers which carry oxygen within their lumens. Blood flows in a relatively slow, generally radial path through the spaced gaps, and encounters a lower pressure drop during oxygenation, such that overall the blood experiences a minimum of unusual stress during its extracorporeal traverse through the assembly of this invention.

The new rigid shell, expansible reservoir and the assembly which includes that new reservoir, a heater and hollow fiber oxygenator, per se, is disclosed in detail and claimed in a separate application which is commonly owned and is being filed concurrently herewith, Ser. No. 350,460.

DESCRIPTION OF THE INVENTION

In accordance with this invention, an expansible blood reservoir is provided having a novel rigid self-supporting, concave shell and an integrally attached flexible membrane or compliant member which forms a variable volume blood reservoir. The reservoir is constructed of transparent or translucent materials and arranged such that the blood concavity is at all times visible to the technician during use for easy observation of the blood level in the reservoir. The reservoir is provided with blood inlet means communicating with the interior of the container which is located so as to facilitate froth or bubble removal through other means integral with the rigid shell and associated with the blood pool in the expansible container at all levels of blood therein. The reservoir is also provided with blood outlet means so constructed with respect to size and location relative to the blood inlet means as to insure a low exit blood flow velocity which is adapted to prevent entrainment of bubbles, or froth, in the blood exiting from the reservoir into the heater.

The assembly of the variable volume reservoir of this invention with a blood heater and hollow fiber oxygenator locates the reservoir on top, with the heater being attached to the lower end of the reservoir and the hollow fiber oxygenator being attached to the lower end of the heater for use in generally vertical array. The rigid nature of the reservoir, heater and oxygenator and the complementary shapes of each component forms an assembly that is easy to handle, and hook up for use in the operating room to a conventional stand, or movable console which may advantageously be provided with a support for receiving the assembly and blood pump means. Such console may also include single means for facile attachment to water supply connections on the rigid shell of the reservoir.

The preferred embodiments of the invention are shown in the drawings which illustrate the best form contemplated for use.

FIG. 1 is a perspective view, in elevation, of the assembly showing the reservoir partially filled with blood, the intermediate heater with a portion broken away showing the coil heater element, and the lower hollow fiber oxygenator;

FIG. 2 is a sectional view taken along line 2—2 of FIG. 3 and looking in the direction of the arrows;

FIG. 3 is a vertical cross-sectional view of the assembly of FIG. 1.

FIG. 4 is a rear elevation view showing preferred connection port locations;

FIG. 5 is a schematic illustrating the preferred blood flow path for use of the assembly of FIG. 1;

FIG. 6 is a schematic illustrating a first alternate blood flow path for use of the assembly of FIG. 1;

FIG. 7 is a schematic illustrating a second blood flow path for use of the assembly of FIG. 1;

FIG. 8 is a cross-sectional view illustrating a modified shape of a rigid shell usable to replace the preferred cylindrical shape illustrated in FIG. 1; and FIG. 9 is a side view in elevation of the assembly of FIG. 1 mounted for use on a preferred form of movable support console.

Referring to the drawings, the oxygenator assembly of this invention, generally designated 10, and as best seen in FIGS. 1, 2 and 3, comprises a rigid shell reservoir generally designated 20, a heater generally designated 40, and a blood oxygenator generally designated 60. Reservoir 20, heater 40 and oxygenator 60 are shown in permanently secured assembly form in the preferred vertical orientation of normal use during surgery. The typical use arrangement is illustrated in FIG. 9 which shows assembly 10 mounted on a preferred type of movable support console generally designated 100, which will be described in detail hereinafter.

As best seen in FIGS. 2 and 3, reservoir 20 comprises rigid shell member 22 and a compliant, flexible membrane member 24. Shell member 22 is shown in its preferred semicylindrical shape for the greater portion of its length and terminates at its upper end in a dome shaped section 23, and at its lower end terminates in an arcuate shaped concave section 25. The rigid rear wall 22 forms an internally rounded concavity that is open and visible to the observer as a semi-cylindrical cavity when looking from the front as shown in FIG. 1. Flexible membrane 24 is formed from a translucent, or preferably from a transparent thin film of a somewhat elastic, stress-resistant material that is blood compatible such as the preferred silastic rubber, or polyvinylchloride, polyethylene, polypropylene or the like.

Membrane 24 is sized and shaped for attachment to the peripheral edges of the concavity in rigid shell reservoir 20 such that it folds into the concavity and rests upon, or overlies, the inner surfaces of lower dome section 25, shell 22 and upper dome section 23 when the reservoir is empty. FIG. 3 illustrates reservoir 20 in a partially filled condition in which blood occupies a portion of the variable volume container defined by rear shell wall 22 and outwardly spaced flexible membrane 24. As the blood volume increases flexible membrane 24 moves farther away from shell 22 to accommodate any variable volume of blood which is desired in the blood container up to and including maximum extension of membrane 24. In the preferred form of shell 22, shown in FIG. 3, section 26 is provided to serve as a support for membrane 24 as it approaches its maximum volume which is represented by dotted line 24'.

Any suitable means for fastening membrane 24 to shell 22 may be employed which insures a liquid tight and air tight connection as the stresses change with increasing, and decreasing quantities of blood in the container during use. As shown in FIGS. 2 and 3 membrane 24 is provided with a peripheral bead 27 which is secured to the side edges of shell 22 and to section 23 at its upper end and to section 25 at its lower end. Bead 27 is received in a peripheral channel 28 located in the peripheral edge surfaces of shell 22, and in a mating channel or slot in overlying flange 29. Flange 29 surrounds and follows the peripheral contour of the concavity in shell 22 and is secured to shell 22 and sections 23, 25 by any suitable means, such as adhesive, heat sealing, etc.

Rigid shell 22 is provided with a venous blood inlet port 30 which during use is connected to a conventional venous drainage line, not shown. Shell 22 has a second venous blood inlet port 32 which during use is connected to a cardiotomy reservoir, not shown. Both inlet ports 30, 32 penetrate rear shell wall 22 adjacent to, but spaced upwardly from the lower end of reservoir 20 and preferably at an upwardly inclined angle from horizontal, or for example, 15° to 60°, to direct the blood entering the reservoir cavity away from blood leaving the cavity through blood outlet means 34. Blood outlet means 34, as shown in FIG. 2, are located in lower dome section 25 adjacent to and slightly spaced rearwardly from the connection between reservoir section 25 and membrane 24. Means 34, as shown, comprises a plurality of elongated apertures 35 in section 25 which are enclosed by blood channel means 36 which extend downwardly and terminate at their lower ends in openings 37 into the manifold 38 of heater 40. A plurality of blood apertures 35 as the outlet path of blood from reservoir 20, as opposed to single outlet, is advantageous because they provide a larger cross sectional area flow of the blood, thus reducing blood flow velocity which minimizes the likelihood of entrainment of gas bubbles in the blood that would eventually require removal before return to the patient. A similar result is obtainable by other constructions as will be readily apparent to one skilled in the art when seeking to provide other forms of blood outlet means, or location, or size of outlet opening relative to size and location of blood inlet openings to prevent undesirable bubble entrainment in the blood exiting from reservoir 20.

To make reservoir 20 readily disengageable from heater 40 and/or blood oxygenator 60, the construction of blood outlet means 34 is contemplated to be modifiable to terminate in a common closed channel member, not shown, that is provided with a single blood outlet.

Rigid shell 22 is provided with means for facilitating removal of bubbles inadvertently introduced from the venous drainage line into the pool of blood in reservoir 20 which is automatically operational and functional at all levels of the blood pool in the reservoir. In its preferred form, the debubbling means is a channel 39 cut into the inner surface of rigid shell wall 22 on the diametrical centerline of the cylindrical concavity and which extends from a point below blood inlet ports 30, 32 upwardly through dome section 23 to gas vent port 81. Suction means attached to port 81 efficiently causes air bubbles to move across the top surface of the blood pool and into channel 39 even though flexible membrane 24 is overlying a part of shell wall 22 and the wall of dome section 23. If desired, more than 1 channel can be used in a similar manner.

Reservoir 20 is provided with an external housing 42 located centrally on the rear surface of rigid shell 22 and extends vertically from the top of dome section 23 to the lower end of heater 40. Housing 42 is integrally attached to shell 22 and joined to rigid molded interconnection section 44 at the lower end of heater 40. Housing 42 provides an enclosure for inlet and outlet blood and water ports, sampling tubes, and rigidifies the assembly into a unitary structure which is easily handled, and hooked up to mobile support console 100. Venous inlet port 30 has a sampling site 31 located on the upper surface of port 30 in the enclosure between shell 22 and housing 42 which is connected by tube 33 to venous sampling stopcock 83. Stopcock 83 is a three-way stopcock which provides one luer port for administration of fluids and drugs into the venous blood stream and another port for taking venous blood samples.

Rigid inwardly tapering section 44, as shown, is permanently attached to housing 42 and to the outer wall 46 of heater 40. Wall 46 is extended, at its upper end portion, by a section 48 which serves to support forward extension section 26 and membrane 24 as blood volume increases in reservoir 20 and functions as an interconnection between heater 40 and reservoir 20. When reservoir 20 is constructed as a separate component with a single blood outlet as above described, wall 48 will be replaced with other suitable connecting means for assembly into an integral unit, if desired.

The outer wall 46 of heater 40 terminates at its upper end in inwardly tapered section 50 which, together with the upper extension 52 of cylindrical wall 54 define blood manifold 38, previously mentioned. The heat exchanger coil 56 is positioned in the annular space 57 and is a conventional helical coil of externally ribbed aluminum tubing provided with water inlet 58 and water outlet 59 which extend through housing 42 and are sealed from annular blood space 57 in conventional manner. A blood outlet port 62 is provided adjacent to the lower end of heater 40 and communicates with the interior of blood annulus 57 and serves to deliver blood to the blood inlet port 64 of blood oxygenator 60.

Blood oxygenator 60, as shown, is of the hollow fiber type which supplies oxygen to, and removes carbon dioxide from, blood flowing on the outside of a plural layer mat of hollow fibers which carry oxygen inside the fiber lumens. Oxygenator 60 comprises an outer cylindrical wall 66, an inner cylindrical core wall 68 which is porous and supports a plural layer mat of hollow fibers 70. The hollow fiber mat 70 terminates at opposite ends in resin tubesheets 71, 73 which seal the mat 70 to the walls 66, 68 in liquid and gas tight relationship and also seals the hollow fibers to each other in the manner of U.S. Pat. No. 3,228,876. Oxygenator 60 is optionally permanently, or disengageably, secured to tapered section 44. The open ends of each of the hollow fibers in mat 70 terminate in the outer planar surface of tubesheets 71, 73. Oxygen enters housing 42 through port 72 and fills the internal reservoir 75 defined by inner walls 54 of heater 40, and flows into each open end of each fiber at tubesheet 71. Oxygen in the fiber lumens follows a helical path downwardly to exit from tubesheet 73 through outlet port 74. Blood entering through port 64 travels upwardly into the hollow core chamber 75 and into the annular space 76 between the inner surface of core wall 68 and the outer surface of flow guide core member 77, thence outwardly through the mat 70 and into the annular space 78 between the inner surface of wall 66 and the outer surface of mat 70. Blood reaching annular space 78, in oxygenated and purified condition, travels outwardly through blood outlet 80 for return to the patient.

Oxygenator 60, is provided with an air bubble vent tube 61 which connects into the top of blood annular space 78 and to stopcock 85 located on the top of housing 42. Stopcock 85 is a three-way stopcock providing one port for taking arterial samples, and another port provided with tubing, not shown, that connects to the cardiotomy reservoir. Air bubbles, inadvertently present in the blood annulus 78 can be removed by suction applied at stopcock 85 of the arterial pump can cause a small continuous stream of oxygenated blood to flow upwardly into the cardiotomy reservoir and thereby automatically and continuously purge air bubbles. Air bubbles which may collect at the upper end of core chamber 75 are periodically, or continuously, ventable through tube 63 and outlet port 65.

FIGS. 5, 6 and 7 illustrate satisfactory blood flow paths which may be used with the assembly of this invention. FIG. 5 shows the preferred flow path which provides venous blood through line 90 into reservoir 20 through blood inlet 30. Blood flows from the blood pool in reservoir 20 through blood outlet 35 into blood manifold 38 in heater 40 and heated blood flows out through heater blood outlet 62, through blood pump 92 into oxygenator 60 through blood inlet port 64, and after purification and oxygenation blood flows out through port 80 and arterial line 94 back to the patient undergoing surgery.

FIG. 6 illustrates an alternate arrangement for hook-up and use of assembly 10. Venous blood flows through line 96 into blood oxygenator inlet 64, from outlet 80 into blood reservoir inlet 30, downwardly into heater 40 and the heated, oxygenated blood passes through pump 97 and arterial line 98 back to patient. This arrangement keeps all components at low pressure, requires low blood phase pressure drop in the oxygenator and low gas phase pressure drop to prevent gas embolization across the walls of the gas permeable membrane in mat 70.

FIG. 7 shows a flow path similar to that of FIG. 5 except that a blood pump 99 is located in the return to patient arterial line 101. This arrangement permits flow directly from reservoir 20 to heater 40 to oxygenator 60 through line 102 or internally by redirecting blood outlet 62 to feed blood to the upper end portion of core chamber 75. This arrangement requires low, consistent blood phase and gas phase pressure drops to insure against gas embolization in the oxygenator.

FIG. 8 illustrates an alternate rigid reservoir shell wall configuration which differs from cylindrical wall 22 in having a rounded dish shape with a flattened central section 104, against which flexible membrane 106 overlies when reservoir 20 is empty. When the reservoir is full of blood the contour of flexible membrane 106 assumes the shape shown in dotted lines 106'.

FIG. 9 shows a preferred form of movable console 100 for facile hook-up of the assembly 10 during operating room use. Console 100 comprises preferably a four wheeled base 108, an upright support arm or post 110 having a vertically positionable connector arm 112 supported on upright support 110. Connector arm 112 is provided with an assembly holder 114 equipped with appropriately located and sized connectors for simultaneous connection to water and oxygen port means 58, 59 and 72, and to positively maintain assembly 10 in substantially vertical position during use. Water lines 76 are connected to the assembly holder water connectors 78 and can be left in place between procedures if desired. Assembly holder 114 pivots at its junction with connector arm 112 and the connector are can be rotated and moved vertically at its junction with the post 110 to allow the assembly to be positioned as desired.

We claim:

1. A blood reservoir comprising
   (1) a self-supporting member having a rigid shell portion defining a concavity opening inwardly into a reservoir chamber and defining a rigid inner wall thereof;
   (2) flexible membrane means secured by a liquid-tight seal to said shell portion around the periphery of said concavity in overlying relationship to said concavity and forming, with said inner wall, said reservoir chamber, whereby said reservoir chamber comprises a variable volume liquid tight chamber;
   (3) said flexible membrane means interfitting with said overlying the inner wall of said concavity when said chamber is empty amd movable to variable positions outwardly from said inner wall as liquid enters said chamber between said inner wall and membrane means, and
   (4) blood inlet and outlet means integral with said rigid shell portion of said concavity and communicating with said chamber.

2. A blood reservoir in accordance with claim 1 wherein said rigid shell portion comprises an elongated semi-circular cylindrical section having an upper end terminating in a dome shaped section, said inlet and outlet means are positioned in spaced apart locations adjacent to the lower end of said cylindrical section, and a bubble removal port is located in said dome shaped section adjacent its upper extremity.

3. A blood reservoir in accordance with claim 1 or claim 2 wherein said rigid shell portion includes at least one channel in the inner wall thereof which extends from adjacent to the lower end to adjacent to the upper end of said chamber.

4. A blood reservoir in accordance with claim 1 wherein said rigid shell portion comprises an elongated semi-circular cylindrical section having upper and lower ends terminating in integral dome shaped sections, said inlet and outlet means are positioned in spaced apart locations in the wall of said lower dome shaped section, said lower dome shaped section providing underlying support for said membrane means as the volume of said chamber varies, and a bubble removal port is located in said upper dome shaped section.

5. A blood reservoir in accordance with claim 1 wherein said rigid shell portion comprises an elongated semi-circular cylindrical section having upper and lower ends terminating in integral dome shaped sections, said inlet and outlet means are positioned in spaced apart locations in the wall of said lower dome shaped section, a bubble removal port is located in said upper dome shaped section, said blood outlet means comprises a plurality of blood receiving aperatures adjacent the lower end of said chamber that are sized and located so as to minimize entrainment of bubbles in the blood exiting from said chamber.

6. A blood reservoir in accordance with claim 1 wherein said rigid shell portion comprises an elongated semi-circular cylindrical section having upper and lower ends terminating in integral dome shaped sections, said inlet and outlet means are positioned in said lower dome shaped section in spaced apart adjacency, a bubble removal port is located in said upper dome shaped section adjacent the upper extremity thereof, said rigid shell portion having a channel depressed in the inner wall of said cylindrical section and located in the mid-portion thereof and extending from said bubble removal port to a point closely adjacent to the lower end of said chamber, and said bubble removal port is in communication with said depressed channel.

7. A blood reservoir in accordance with claim 1 wherein said rigid shell portion and said flexible membrane means are fabricated from material ranging in light transmitting properties from transparent to translucent.

8. A blood reservoir in accordance with claim 1 wherein said inner wall has a rounded shape and said blood outlet means is located adjacent the lower end of said chamber.

9. A blood reservoir in accordance with claim 8 wherein said rigid shell portion comprises an elongated semi-circular cylindrical section terminating in an integral dome shaped section on at least one end thereof.

10. A blood reservoir in accordance with claim 9 wherein said inlet and said outlet means are located in spaced apart locations adjacent to the lower end of said chamber.

11. A blood reservoir as claimed in claim 1 and arranged with a heat exchanger and a blood oxygenator to provide a blood oxygenator assembly,
    said heat exchanger being secured to the lower end of said reservoir, said outlet means being adjacent to the lower end of said chamber and comprising blood inlet means for said heat exchanger adjacent to the upper end of the latter, blood outlet means for discharging heated blood from said heat exchanger,
    said blood oxygenator being secured to the lower end of said heat exchanger and having blood inlet and outlet means.

12. A blood oxygenator assembly in accordance with claim 11 wherein said blood oxygenator is a hollow fiber oxygenator of the type which flows oxygen through the lumens of the hollow fibers and blood over the outside surfaces of said fibers.

13. A blood oxygenator in accordance with claim 11 wherein blood supply means provide venous blood to said reservoir, means transfer blood from said reservoir to the top portion of said heater, means transfer blood from the lower end of said heater to the lower end of said blood oxygenator, and means transfer oxygenated blood from blood exit means adjacent the lower end of said blood oxygenator to a patient.

14. A blood oxygenator in accordance with claim 11 wherein blood supply means provide venous blood to the lower end of said blood oxygenator, means transfer oxygenated blood from exit means adjacent the lower end of said oxygenator to blood inlet means on said reservoir, means transfer oxygenated blood from said reservoir to the top portion of said heater and means transfer heated and oxygenated blood to a patient.

* * * * *